United States Patent [19]

Öhlin et al.

[11] Patent Number: 4,617,009
[45] Date of Patent: Oct. 14, 1986

[54] METHOD AND APPARATUS FOR CENTRIFUGAL BATCH SEPARATION OF BLOOD

[75] Inventors: L. Erik Öhlin, Stocksund; H. Peter Unger, Stockholm; J. Eric Westberg, Lidingö, all of Sweden

[73] Assignee: Seroteknik HG, Stocksund, Sweden

[21] Appl. No.: 637,046

[22] PCT Filed: Nov. 28, 1983

[86] PCT No.: PCT/SE83/00413
§ 371 Date: Jul. 26, 1984
§ 102(e) Date: Jul. 26, 1984

[87] PCT Pub. No.: WO84/02091
PCT Pub. Date: Jun. 7, 1984

[30] Foreign Application Priority Data

Nov. 26, 1982 [SE] Sweden .................. 8206767

[51] Int. Cl.[4] .................. B04B 5/02
[52] U.S. Cl. .................. 494/21; 494/37; 494/45; 604/410
[58] Field of Search .................. 494/1, 4, 10, 21, 37, 494/45; 604/408–410

[56] References Cited

U.S. PATENT DOCUMENTS

| | | | |
|---|---|---|---|
| 3,244,363 | 4/1966 | Hein | 494/1 |
| 3,257,072 | 6/1966 | Reynolds | 494/10 |
| 3,987,961 | 10/1976 | Sinn et al. | 494/45 |
| 4,111,355 | 9/1978 | Ishimaru | 494/45 |
| 4,146,172 | 3/1979 | Cullis et al. | 494/21 |
| 4,266,717 | 5/1981 | Jennings | 494/45 |
| 4,268,393 | 5/1981 | Persidsky | 494/21 |

Primary Examiner—Robert W. Jenkins
Attorney, Agent, or Firm—Hill, Van Santen, Steadman & Simpson

[57] ABSTRACT

Centrifugal batch separation of blood in a closed collapsible container is carried out by placing the container in a rigid casing in which the container is divided into two or more sections in that the casing constricts the container at one or more predetermined positions between the ends of the container. The casing with the container therein is then centrifuged, a gap-like passage between the container sections permitting rearrangement of the contents of the container so that each section will accommodate a blood fraction. After the centrifugation the fractions are isolated from each other. The volume of the cavity within the casing accommodating the radially outermost container section is matched with the hematocrit and the total blood volume by means of filler bodies.

29 Claims, 11 Drawing Figures

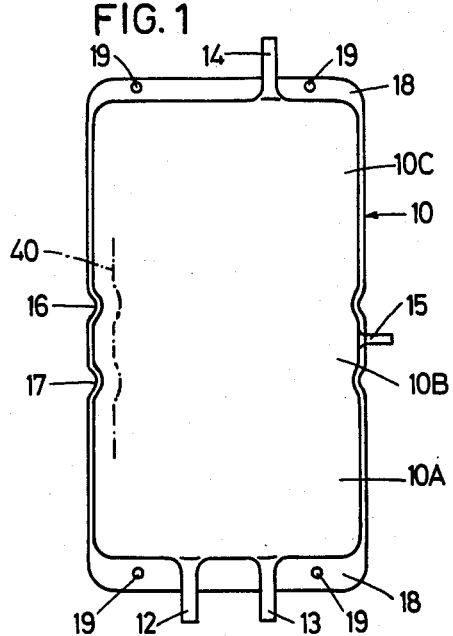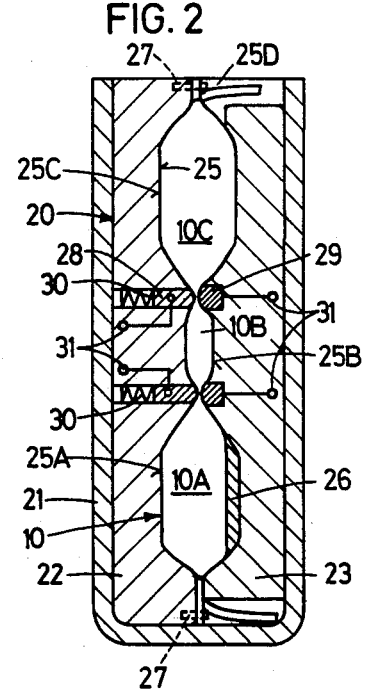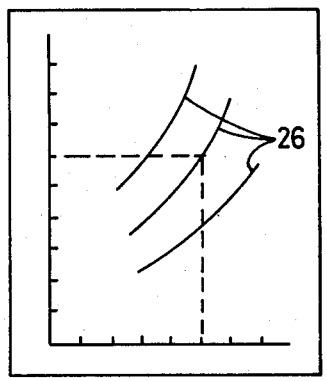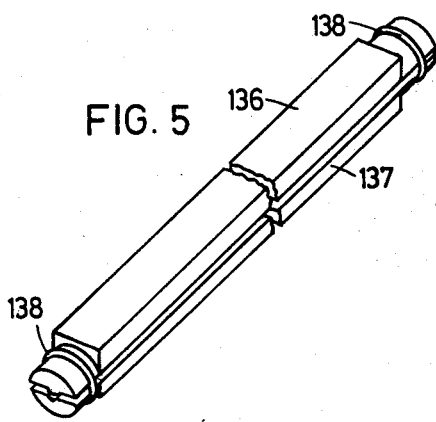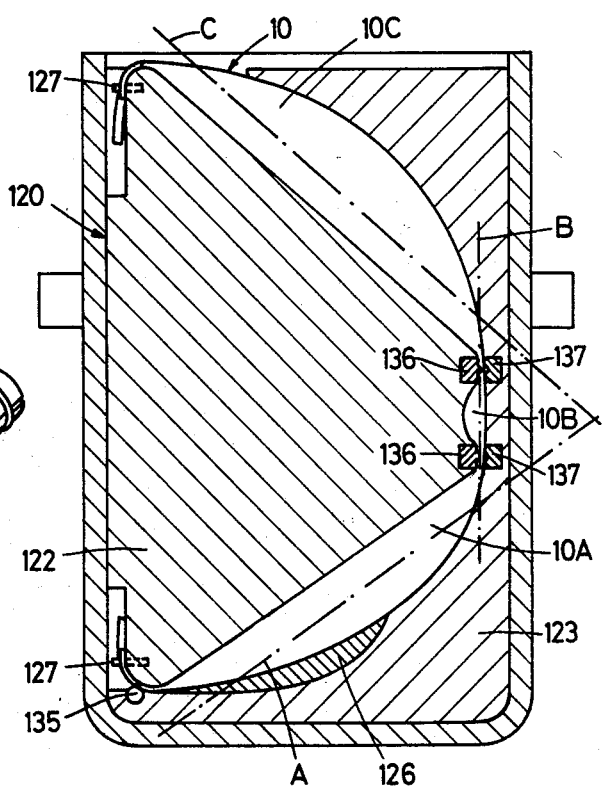

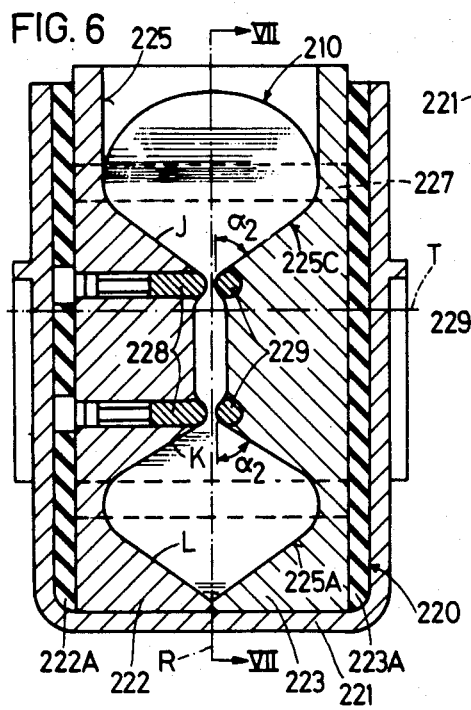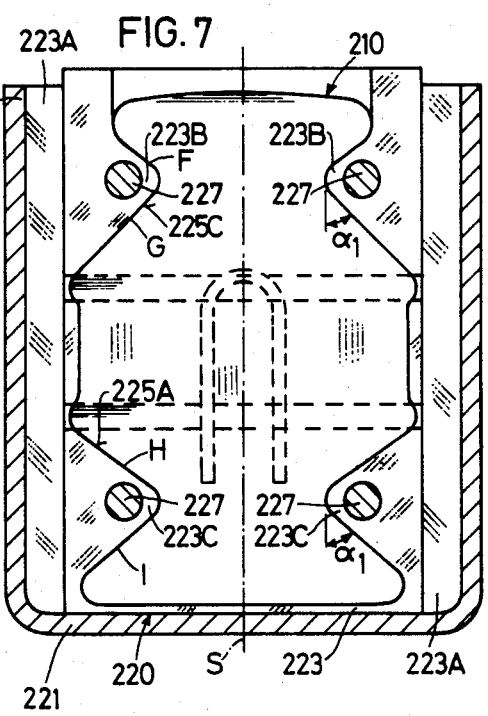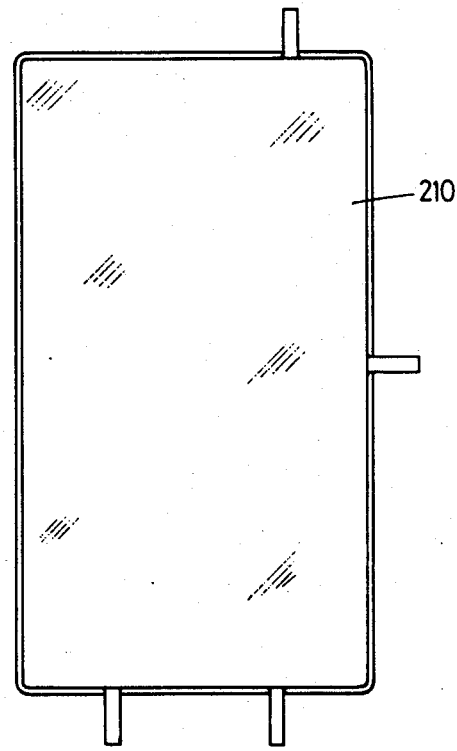

METHOD AND APPARATUS FOR CENTRIFUGAL BATCH SEPARATION OF BLOOD

BACKGROUND OF THE INVENTION (a) Field of the Invention

This invention relates to centrifugal separation of blood, namely, centrifugal batch separation of blood in a closed collapsible blood container and subsequent isolation of the centrifugally formed fractions.

(b) Prior Art

The presently predominant technique for centrifugal batch separation of blood comprises use of a collapsible main container holding whole blood to be separated and one or more initially empty auxiliary containers connected with the main container through flexible conduits.

In the most straightforward case, the blood is separated into a heavier fraction comprising the main portion of the erythrocytes (the red blood cells) of the batch of blood confined in the main container, and a lighter fraction mainly consisting of plasma. A single auxiliary container is used in this case. When the centrifugation is to be carried out, the filled main container and the auxiliary container are placed in a centrifuge in which the container assembly is centrifuged until the blood has been separated into the two fractions. Then the containers are carefully removed from the centrifuge and the plasma fraction is transferred to the auxiliary container through the connecting conduit by subjecting the main container to an exterior pressure.

Other cases may comprise separation of the blood into additional fractions, such as a fraction constituting the so-called buffy-coat, which includes the main portion of the platelets and is of a density lower than that of the erythrocyte fraction but higher than that of the plasma fraction. Consequently, upon completed centrifugation, the buffy-coat fraction, which amounts to a very small portion, one percent or so, of the total blood volume, is positioned between the plasma fraction and the erythrocyte fraction in the container. For the buffy-coat fraction a second auxiliary container is used into which that fraction is squeezed after the plasma fraction has been transferred to the first auxiliary container and the connecting conduit of the latter has been closed.

In actual practice it is very difficult or indeed impossible after the centrifugation to prevent intermixing of the fractions before the transfer into the auxiliary container or containers. When the container assembly is being lifted from the centrifuge and the main container is subjected to exterior pressure during the handling, its shape is unavoidably altered so that undesired flow within the fractions and shifting of portions of the fractions in one direction or other within the container take place, resulting in indistinct separation of the fractions. Consequently, each fraction is more or less contaminated with portions of the adjoining fraction.

Also known, but not applied in actual practice, in connection with centrifugal batch separation is a technique involving use of a single elongated blood container which is filled with a predetermined quantity of blood and then placed in a centrifuge rotor and centrifuged until the blood has been divided into two or more fractions.

In order to isolate the various fractions in the container from each other upon completion of the centrifugation, the blood container is pinched in the region of the interface of adjoining fractions, and it is also known to render the isolation achieved through the pinching permanent by welding the container walls together at the pinched region or regions. Then the blood container may be severed at the welded region or regions so that separate container sections containing different fractions are obtained.

In this case it is also virtually impossible to avoid intermixing of the fractions before they have been isolated from each other by pinching and, as the case may be, welding the container walls, because the handling during the removal of the container from the centrifuge and the pinching unavoidably result in flow within the fractions and displacement of the fractions within the container.

SUMMARY OF THE INVENTION

An object of the invention is to make it possible in a simple way to isolate the fractions from each other with a minimum of intermixing of adjoining portions of the centrifugally formed fractions.

Among the characterising features of the invention is that the closing of the passages between the container compartments is effected while the container is in the casing, preferably while the blood is still subjected to a certain centrifugal force, and without substantial alteration of the shape of the container. To this end, before the centrifugation is carried out the container is constricted at the regions where the interfaces of the fractions will be located, so that only a relatively small movement of the container walls is required for closing the passages between adjoining container sections holding different fractions.

In order that the closing operation (aiming at isolating the erythrocyte fraction, i.e., the fraction that occupies the radially outermost position in the centrifuge, from the inwardly next adjacent fraction), may always be effected exactly at the desired position, at the interface of the fractions, even if the volume of the batch of blood confined in the container and the hematocrit of the blood (the ratio of the erythrocyte volume to the total volume) varies from batch to batch, the total volume and the hematocrit of each batch is determined before the centrifugation is carried out, whereupon, if necessary, the volumetric capacity of the container section intended for receiving the erythrocyte fraction is adjusted according to the product of the hematocrit and the total volume. The adjustment of the volumetric capacity is effected such that the closing is always effected at the same position on all containers.

DESCRIPTION OF THE DRAWINGS

FIG. 1 is a plan view of an empty blood container for use in carrying out the method according to the invention;

FIG. 2 is a view in longitudinal section of the container of FIG. 1 when filled with blood and inserted in a cassette-like casing which in turn is inserted in a cup-shaped receptacle forming part of a centrifuge rotor;

FIG. 3 shows a nomogram which may be used for the selection of a filler body for adjusting the volumetric capacity of the container section receiving the erythrocyte fraction;

FIG. 4 shows an alternative embodiment in an illustration resembling FIG. 2;

FIG. 5 shows one of a pair of clamps forming part of the embodiment shown in FIG. 4 and serving the purpose of pinching the container;

FIG. 6 shows a further embodiment in an illustration resembling FIG. 2;

FIG. 7 is a view in cross-section on line VII—VII of the device shown in FIG. 6;

FIG. 8 is a plan view corresponding to FIG. 1 showing the container used in FIGS. 6 and 7.

DESCRIPTION OF THE PREFERRED EMBODIMENTS

Figure 9:
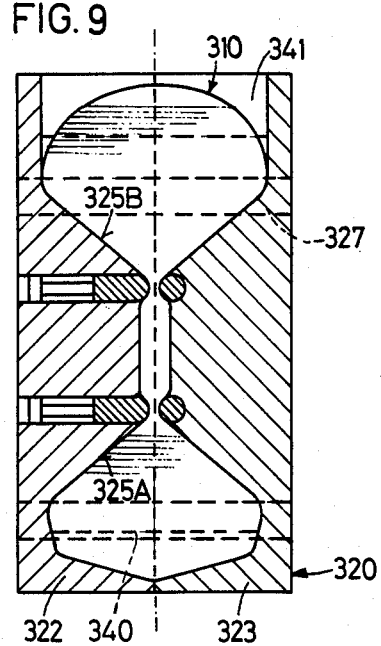
FIGS. 9 and 10 are illustrations resembling respectively FIGS. 6 and 7 of a modified shape of the cassette-like casing.

The blood container 10 shown in FIG. 1 is made in accordance with known techniques by welding together two rectangular pieces of plastic film. Integrated with the container are a number of flexible conduits for introducing blood and any additives (such as anticoagulant) and for withdrawing blood components, namely, a filling conduit 12 through which blood is introduced into the container, en erythrocyte conduit 13 through which the erythrocyte fraction may be withdrawn, a plasma conduit 14 through which the plasma fraction may be withdrawn, and a buffy-coat conduit 15 through which the buffy-coat fraction may be withdrawn.

In the condition shown in the figure, in which the container is empty with the two film pieces im face-to-face engagement throughout their length and width, the intermediate portion of the container has a pair of "waists" 16 and 17 on opposite sides of the region where the buffy-coat conduit 15 is connected. These waists are positioned where after completed centrifugation the blood fractions are isolated from each other. They also form a transition between three sections 10A, 10B and 10C of the container. Of these sections, the two outer or end sections 10A and 10C are of approximately the same size and are intended to hold respectively the erythrocyte fraction and the plasma fraction. The intermediate section 10B, which is intended to hold the buffy-coat fraction, is very small compared with the two other sections.

The container is intended to be filled with about 500 ml of blood and is dimensioned to be able to receive that quantity of blood without becoming firmly expanded.

As shown in FIG. 1, the container is elongated, in that its length is considerably greater than its width. Upon filling, the width will be somewhat reduced while the length will remain substantially unchanged. When the container is filled, each of the two outer sections 10A and 10C is approximately square and its thickness is small compared to its length and width.

Each end of the container 10 has a tab 18 formed with a pair of mounting holes 19.

When the batch of blood introduced into the container 10 is to be separated, the container is inserted in a flat cassette-like casing 20 shown diagrammatically in FIG. 2 which is then inserted in a cup-shaped receptacle 21. This receptacle forms part of a centrifuge rotor, not shown, in which the receptacle is positioned eccentrically and arranged such that during the centrifugation its longitudinal axis or central plane includes an angle with the axis of rotation of the rotor.

The casing 20 is rigid so that it is capable of carrying the forces resulting from the centrifugation without undergoing substantial deformation. Essentially, the casing comprises two halves 22 and 23 which can be coupled together and which define between them a container receiving chamber 25 of the flat cross-sectional shape shown in FIG. 2. The extension of the container receiving chamber transversely of the plane of FIG. 2 is matched with the width of the filled container 10. In its central region, the container receiving chamber 25 has a pair of constrictions dividing the chamber into three compartments 25A, 25B, 25C for receiving respectively the container sections 10A, 10B and 10C.

When the container 10 is inserted in the casing and the two casing halves are joined together, substantially the entire surface of each container wall engages the casing surface defining the container receiving chamber 25; only at the end of the casing positioned at the mouth of the receptacle 21 is there a region 25D where the container wall is not firmly supported by the casing.

Within the compartment 25A of the container receiving chamber 25 which is closest to the bottom of the receptacle 21, a portion of the casing wall engaging the container 10 is formed by a removable filler body 26. This filler body 26 is sized such that the volume accommodated in the compartment 25A or, more precisely, in the container section 10A received therein, as nearly as possible equals the combined volume of the erythrocytes contained in the blood, that is, the product of the hematocrit and the total volume of the blood in the container. Thus, before the blood container is placed in the casing, the volume and the hematocrit must be determined and an appropriate filler body 26 positioned in the container receiving chamber of the casing.

The selection of the filler body may be made with the help of the nomogram of FIG. 3 where the vertical axis represents the hematocrit while the curves 26 represent different volumes. The filler body best suited for the occasion is the filler body marked on the horizontal axis vertically below the intersection of the applicable volume curve and a horizontal line drawn from the determined hematocrit on the vertical axis.

The volume of the compartment 25A of the container receiving chamber 25 may also be adjusted in ways other than by insertion of different filler bodies. For example, a portion of a wall defining the compartment may be movable and adjustable by means of an adjusting device on the casing. Naturally, it is also possible to use casings of non-adjustable volume, the matching with the determined blood volume being made by selection of a casing the compartment 25A of which is of the appropriate volume.

When the container 10 is inserted in the casing 20, the holes 19 of the container tabs are engaged over a number of pegs 27 secured to the casing half 22. The conduits 12 to 15 and their connectors are engaged in recesses in one or both of the casing halves.

As the casing halves are brought together with the container 10 positioned in the container receiving chamber 25, the two opposed container walls are clamped together across the width of the container at the waists 16 and 17. This pinching or clamping takes place by the action of two pressure bars 28 which are movably mounted in the casing half 22 and are urged by springs 30 toward a pair of stationary backing bars 29 in the other casing half.

The pressure bars 28 and the backing bars 29, which in the illustrated embodiment extend across the entire container receiving chamber 25, are also adapted to serve as welding or heat sealing jaws and to this end are provided with electrical heaters, high frequency heating electrodes or other suitable heat sealing means and associated terminals 31 for a separate source of electrical energy. For the sake of simplicity, these terminals are only symbolically shown in FIG. 2.

During the centrifugation the centrifugally produced hydrostatic pressure within the container 10 causes a slight displacement of the pressure bars 28 outwardly against the spring loading. As a consequence, a gap extending across the width of the container and having a width of one or a few millimeters will be formed at each waist 16, 17 of the container, so that the three container sections 10A, 10B, 10C are placed in open communication. The contents of the container can thereby be rearranged to form three main fractions, namely, an erythrocyte fraction in the radially outermost container section 10A, a buffy-coat fraction in the intermediate container section 10B and a plasma fraction in the radially innermost container section 10C.

As the rotational speed of the centrifuge rotor is reduced after the various fractions have been formed, the springs 30 will again close the gaps between the container sections when a predetermined speed controlled by, for example, the spring force is reached. The resulting movement of one of the container walls is very small and restricted to the region immediately adjacent the pressure bars 28, so that the centrifugally produced separation of the blood into fractions is disturbed very little.

After the centrifuge has stopped, the casing 20 is removed from the receptacle 21, whereupon the terminals 31 are connected to a source of electrical energy for welding or heat sealing together the opposed container walls at the waists 16 and 17, so that the isolation of the fractions from each other resulting from the pinching of the container walls is made permanent. The container can then be taken out of the casing and, if desired, cut off at the waists so that each container section 10A, 10B, 10C forms a separate container.

In the embodiment shown in FIG. 4 the three flat container sections 10A, 10B and 10C are disposed in a casing 120 such that their general planes include an angle with respect to each other; in the figure the general planes A, B and C are represented by phantom lines. The general planes A and C of the container sections 10A and 10C are disposed such that they include an angle of 30° to 60° C. with respect to the direction of the centrifugal force during the centrifugation, while the general plane B of the container section 10B is oriented substantially in the direction of the centrifugal force. The angled position of the container sections 10A and 10C reduces the requirement for space in the direction of the centrifugal force so that a commercially available centrifuge having pivoted container receptacles can be used, and at the same time the angle effect results in an efficient fractionation. As a consequence of the disposition of the container section 10B in the direction of the centrifugal force, a great distance of separation in the container compartment is obtained.

As shown in FIG. 4 the casing 120 is formed by two halves 122 and 123, which are joined at a hinge 135. The container 10 is again secured to a number of pegs 127 on the casing half 122, but instead of pinching devices permanently positioned in the casing there is a pair of pinch bars 136, 137 which are loosely inserted in recesses in the casing halves 122 and 123. These pinch bars are positioned in the casing on opposite sides of the blood container 10 at the container waists 16 and 17 and extend across the width of the container. They may be unbiassed or biassed towards the container by resilient members. As in the preceding embodiment, gap-like passages are opened between the sections during the centrifugation, the opening of the passages taking place under the action of the hydrostatic pressure. If the pinch bars are unbiassed, the passages are closed upon completion of the centrifugation by applying a pair of clamping rings 138 over the ends of the pinch bars, see FIG. 5.

At least in the embodiment shown in FIG. 2 the closing of the passages, and consequently the isolation of the fractions from each other, is effected while the centrifuge rotor is spinning, that is, while the centrifugal force is still contributing to maintaining the separation into fractions. However, it is within the scope of the invention to effect the closing after the centrifuge rotor has stopped and the casing has been removed. Thus, it is not necessary before the container has taken out of the casing to clamp or pinch opposed container walls until they engage each other. On the other hand, the closing has to take place while the container is in the casing and without the container walls undergoing large relative movements. If the closing is not effected automatically by resilient pinching devices or in a similar way, the casing, after it has been taken out of the centrifuge, may be engaged with a suitable auxiliary device effecting the closing before the casing is opened and the container is taken out.

Preferably the various filler bodies 26, 126 for the erythrocyte compartment of the container receiving chamber 25, 125 are dimensioned so that with proper selection of the filler body the interface between the erythrocyte fraction and the buffy-coat fraction is always positioned radially inwardly of the outer pinching position. In corresponding manner the radially inner pinching position is located such that it is ensured that substantially all platelets will be confined in the buffy-coat section.

In the embodiments discussed above by way of example the passages at the blood container waists 16 and 17 extend across substantially the entire width of the container. However, it is within the scope of the invention to shape the container such that the passages only extend across a portion of the container. This can be done by welding together the opposed container walls over a larger or smaller portion of the width of the container when the container is produced.

Further modifications and additions can be made within the scope of the invention. For example, the blood container can be modified to suit the so-called SAG system. To that end the blood container is provided adjacent to the erythrocyte section 10A with a closed container section filled with SAG solution (saline, adenine and glucose) from which, upon completion of the centrifugation and isolation of the erythrocyte fraction, the solution is transferred to the erythrocyte section to be mixed with the erythrocytes therein. The container section containing the SAG solution is folded back when the blood container is inserted in the casing so that it does not occupy any additional radial space.

As a further possible modification a small portion of the plasma fraction, which is free from blood cells, is transferred to the erythrocyte section after the centrifugation in order to make the erythrocyte concentrate therein more fluid. To this end the blood container 10 may be provided with an internal conduit one end of which is in constant open communication with the erythrocyte section 10A and the other end of which is in constant open communication with the plasma section 10C. Such a conduit has been indicated in phantom lines at 40 in FIG. 1. The closing of the passages between the container sections is effected in such a way that a certain amount of plasma may be squeezed over from the plasma section into the erythrocyte section by way of the conduit, which can then be closed, such as by welding at the passages.

The possibility of transferring plasma through the conduit may be realized in various ways. For example, in the embodiments of FIGS. 2 and 4 the pressure bars 28 or 29 or the pinch bars 136 or 137 may be provided with recesses at the points where the conduit is situated during the centrifugation.

In order that the required space in the direction of the centrifugal force may be reduced and in order that creasing or stretching of the container material may be avoided, the embodiment shown in FIG. 4 may be replaced by an embodiment based on the arrangements diagrammatically shown in FIGS. 6 to 10. A characterising feature of these arrangements is that the thickness of the filled container, that is, its largest horizontal dimension as measured in FIG. 6, is substantially larger than the corresponding dimension in FIG. 2.

In the embodiment of FIGS. 6 and 7 a blood container 210 in a manner similar to that shown in FIG. 2 is enclosed in a cassette-like casing 220 during the centrifugation, which casing is inserted in a cup-like receptacle 221 forming part of a centrifuge rotor, not shown, in which the receptacle is pivotable about a horizontal axis. This axis is indicated at T in FIG. 6.

The casing 220 is again rigid and formed of two halves 222 and 223 which can be joined and clamped together and which define a container receiving chamber 225 the shape of which is assumed by the filled container 210 when it is enclosed in the casing. The casing halves 222 and 223 are provided with a pair of movable bars 228 and stationary backing bars 229 substantially corresponding to the pressure bars and the backing bars of FIG. 2.

To the outer side of the casing halves 222 and 223 a lining 222A and 223A of an elastomeric material having a density greater than that of blood is applied. When the casing halves are joined together but free from the action of the centrifugal force, the casing 222 fits the receptacle 221 with a clearance that is just about sufficient to permit ready insertion and removal of the casing from the receptacle. When the casing is in the receptacle and acted on by the centrifugal force, the lining material will be slightly displaced inwardly in the receptacle and thereby cause the casing halves to be clamped together. Naturally, the lining may also be applied to the inner side of the receptacle.

One casing half 222 is provided with four parallel clamping and guiding pins 227 extending into the other casing half 223. These guiding pins serve the purpose of properly locating the casing halves relative to each other when the halves are joined together and to holding, in cooperation with clamping elements (not shown), the halves clamped together.

Each guiding pin 227 passes through a ridge formation provided in the casing halves 222 and 223 and having a generally triangular cross-section. These ridge formations are shown at 223B and 223C in FIG. 7 for the casing half 223. The flanks F, G, H, I of these ridges form a support for the portions of the container 210 situated between, on the one hand, each ridge crest, and, on the other hand, the adjacent container end and the adjacent pair of pressure and backing bars. These flanks, which need not necessarily be of the illustrated flat shape, include an angle $\alpha_1$ (FIG. 7) with one longitudinal central plane S of the casing which is about as large as the angle $\alpha_2$ between the central plane R perpendicular to the plane S and the surfaces J, K, L which constitute wall surface portions of the upper compartment 225C and the lower compartment 225A of the container receiving chamber. The angles $\alpha_1$ and $\alpha_2$ should be as large as possible but may not be so large that the blood cells tend to stick on the inclined container surfaces. The shape of the surfaces F to L and the angles must be chosen such that the perimeter of the container receiving chamber as measured in each chamber cross-section parallel to the axis T is nearly equal to the container perimeter at the same cross-section.

Because of the illustrated and described shape of the container with reduction of the width of the container in two orthogonal directions, the cross-sectional area of the container can be maximized so that the length of the casing can be minimized. This can be done without consequent great risk of an undesired creasing and stretching of the container material and without the inclined surfaces including so large an angle with the direction of the centrifugal field that the blood cells tend to stick.

Apart from the above-discussed differences the embodiment of FIGS. 6 to 8 is similar to the embodiment of FIG. 2 as far as the essential elements are concerned.

Figure 10:
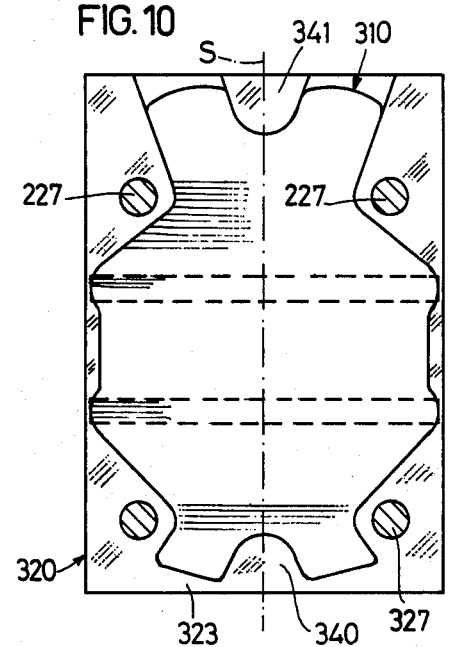
Figure 11:
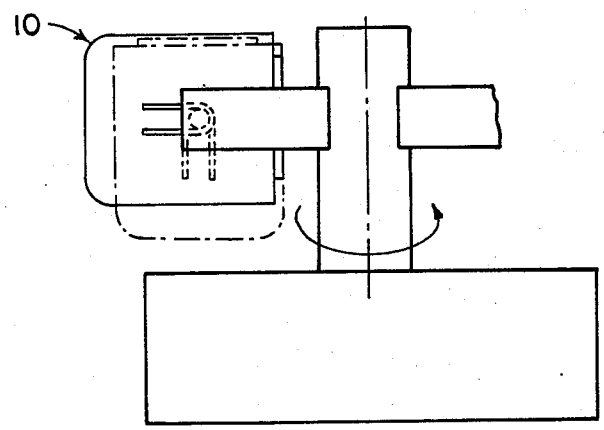
FIG. 11 shows the eccentric positioning of the container with respect to the rotational axis of a diagrammatically illustrated centrifuge.

With the modification of the embodiment of FIGS. 6 to 8 shown in FIGS. 9, 10 the space requirement in the direction of the centrifugal force can be further reduced, and at the same time an additional shortening of the centrifuging distance at the central planes R and S and reduction of the risk of creasing can be achieved. For the sake of simplicity, FIG. 9 only shows a pair of parts 322 and 323 of a casing 320 and a container 310 placed between these parts.

The main difference between the construction shown in FIGS. 9, 10 and the construction shown in FIGS. 6 to 8 is that the casing 320 formed by the parts 322 and 323 has, in a lower compartment 325A of the container receiving chamber, a ridge-shaped filler body 340 and a similar filler body 341 in an upper compartment 325B. The two filler bodies 340 and 341 extend across the container receiving chamber parallel to the guide pins 327 and symmetrically with respect to the central plane S. Through selection of filler bodies 340 of different sizes the volume of the lower compartment 325A of the container receiving chamber may be matched in the above-described manner with the volume and hematocrit of the blood to be separated. Naturally, positions and shapes of the filler bodies other than those shown may be used.

The container 310 used in FIGS. 9, 10 resembles the blood container of FIGS. 6 to 8 apart from the fact that the end portions are slightly tapered.

The modifications and additions explained above with reference to FIGS. 1 to 5 may be made also in the embodiments shown in FIGS. 6 to 10.

As a further modification of the embodiments of FIGS. 6 to 10 the upper and the lower compartment of the container receiving chamber may be shaped as a tetrahedron one end of which extends along the adjacent pair of pressure and backing bars, that is, in the central plane R, while a further edge at the end of the container extends in the central plane S.

In the above-described embodiments the blood container is constricted at two positions so that the buffy-coat fraction may be isilated from the erythrocyte and plasma fractions. However, it is quite possible and within in the scope of the invention to provide a single constriction. This may be the case when carrying out so-called plasmapheresis, for example, when blood plasma is to be separated from whole blood, the blood cells being returned to the donor.

We claim:

1. A method for centrifugal batch separation of blood into fractions of different densities, comprising;
   (a) confining a quantity of blood in an elongated closed container having walls of flexible sheet material;
   (b) placing the container with the blood therein in a rigid casing;
   (c) by means of constriction means within the casing causing the container to be divided into a plurality of sections by forming a container constriction in the opposite container walls extending across the width of the container, one of said sections being an end section for receiving the fraction of the highest density and having a volume determined by the shape and dimensions of the casing; said container constriction forming a flow passage between said sections;
   (d) placing the casing with the container in an eccentric position in a centrifuge and centrifuging it with the end of the container remote from said end section in a radially inner position and said end section in a radially outer position to cause stratification of the blood into said fractions with the interface of adjoining fractions oriented transversely of the longitudinal direction of the container; and
   (e) isolating the fractions from each other within the container by pinching the container along said container constriction to close said flow passage without substantially changing the shape of the container.

2. A method according to claim 1, the total blood volume of the individual container sections being varied by changing the volumetric capacity of the cavity within the casing which accommodates the radially outermost container section.

3. A method according to claim 2, the hematocrit of the blood being determined and the volume of the cavity of the casing which accommodates the container section which is radially outermost during the centriguation being adjusted to a value related to the product of the hematocrit and the total volume of the blood in the container.

4. A method according to claim 2, said opposite container walls being clamped together to close said flow passage when the container is positioned in the casing, the thus closed flow passage being permitted to open against a constantly present closing force under the influence of the hydrostatic pressure within the container and/or under the influence of the centrifugal force.

5. A method according to claim 2, the isolation of the fractions being rendered permanent by welding together the said opposite container walls at the flow passage while the container is in the casing.

6. A method according to claim 2, at least one of the container sections being arranged to include an angle with the other container section or sections when the container is in the casing.

7. A method according to claim 1, the hematocrit of the blood being determined and the volume of the cavity of the casing which accommodates the container section which is radially outermost during the centrifugation being adjusted to a value related to the product of the hematocrit and the total volume of the blood in the container.

8. A method according to claim 7, said opposite container walls being clamped together to close said flow passage when the container is positioned in the casing, the thus closed flow passage being permitted to open against a constantly present closing force under the influence of the hydrostatic pressure within the container and/or under the influence of the centrifugal force.

9. A method according to claim 7, the isolation of the fractions being rendered permanent by welding together the said opposite container walls at the flow passage while the container is in the casing.

10. A method according to claim 7, at least one of the container sections being arranged to include an angle with the other container section or sections when the container is in the casing.

11. A method according to claim 1, the isolation of the fractions being rendered permanent by welding together the said opposite container walls at the flow passage while the container is in the casing.

12. A method according to claim 11, at least one of the container sections being arranged to include an angle with the other container section or sections when the container is in the casing.

13. A method according to claim 1, at least one of the container sections being arranged to include an angle with the other container section or sections when the container is in the casing.

14. A method according to claim 1, said opposite container walls being clamped together to close said flow passage when the container is positioned on the casing, the thus closed flow passage being permitted to open against a constantly present closing force under the influence of the hydrostatic pressure within the container and/or under the influence of the centrifugal force.

15. A method according to claim 14, the isolation of the fractions being rendered permanent by welding together the said opposite container walls at the flow passage while the container is in the casing.

16. A method according to claim 14, at least one of the container sections being arranged to include an angle with the other container section or sections when the container is in the casing.

17. A device for use in centrifugal batch separation of blood into fractions of different densities, the blood being contained in an elongated closed blood container having walls of flexible sheet material and filled with a predetermined discrete volume of the blood, comprising:

A rigid, openable casing adapted to be removably mounted in an eccentric position on a centrifuge rotor, said casing defining an elongated container-receiving chamber adapted to confine therein, and to support the container substantially unyieldingly, the container-receiving chamber comprising two end compartments receptive of opposed end sections of the container and separated by a constriction extending transversely across the width of the container-receiving chamber adjacent to the central portion thereof, the constriction being adapted to define a narrow passage of communication within the container between said end compartments.

18. A device according to claim 17, said constricting means comprising at least one pinching device extending across the container-receiving chamber and adapted to engage and pinch the container at the constriction.

19. A device according to claim 18, said end compartments of the container-receiving chamber being in the form of flat pockets in planes lying at an angle with one another.

20. A device according to claim 17, said end compartments of the container-receiving chamber being in the form of flat pockets in planes lying at an angle with one another.

21. A device for use in centrifugal batch separation of blood into fractions of different densities, the blood being contained in an elongated closed blood container having walls of flexible sheet material and filled with a predetermined discrete volume of the blood, comprising:
a rigid, openable casing adapted to be removably mounted in an eccentric position on a centrifuge rotor, said casing defining an elongated container-receiving chamber adapted to confine therein, and to support the container substantially unyieldingly, the container-receiving chamber comprising two end compartments receptive of opposed end sections of the container and separated by a constriction extending transversely across the width of the container-receiving-chamber adjacent to the central portion thereof, the constriction being adapted to define a narrow passage of communication within the container between said end compartments, said casing, within a zone thereof adapted to accommodate a container section for the densest fraction, being adjustable in respect of the volumetric capacity of said zone.

22. A device according to claim 21, said end compartments of the container-receiving chamber being in the form of flat pockets in planes lying at an angle with one another.

23. A device according to claim 21, the width of each end compartment of said container-receiving chamber, as taken in one of two orthogonal lateral projections, increasing gradually in a direction away from said constriction over a region adjoining said constriction and, as taken in the other of said lateral projections, increasing in a direction away from said constriction over said region, the perimeter of said container-receiving chamber, as taken in planes parallel to the directions of projection, being substantially the same as the perimeter of the blood container as taken at the same planes.

24. A device for use in centrifugal batch separation of blood into fractions of different densities, the blood being contained in an elongated closed blood container having walls of flexible sheet material and filled with a predetermined discrete volume of the blood, comprising:
a rigid, openable casing adapted to be removably mounted in an eccentric position on a centrifuge rotor, said casing defining an elongated container-receiving chamber adapted to confine therein, and to support the container substantially unyieldingly, the container-receiving chamber comprising two end compartments receptive of opposed end sections of the container and separated by a constriction extending transversely across the width of the container-receiving chamber adjacent to the central portion thereof, said constriction being adapted to define a narrow passage of communication within the container between said end compartments, a constricting means comprising at least one pinching device extending across the container-receiving chamber and adapted to engage and pinch the container at the constriction, heat sealing means disposed adjacent to a said pinching device, and means on said casing for connecting said heat sealing means to a source of electrical energy.

25. A device according to claim 24, said end compartments of the container-receiving chamber being in the form of flat pockets in planes lying at an angle with one another.

26. A device according to claim 24, the width of each end compartment of said container-receiving chamber, as taken in one of two orthogonal lateral projections, increasing gradually in a direction away from said constriction over a region adjoining said constriction and, as taken in the other of said lateral projections, increasing in a direction away from said constriction over said region, the perimeter of said container-receiving chamber, as taken in planes parallel to the directions of projection, being substantially the same as the perimeter of the blood container as taken at the same planes.

27. A device for use in centrifugal batch separation of blood into fractions of different densities, the blood being contained in an elongated closed blood container having walls of flexible sheet material and filled with a predetermined discrete volume of the blood, comprising:
a rigid, openable casing adapted to be removably mounted in an eccentric position on a centrifuge rotor, said casing defining an elongated container-receiving chamber adapted to confine therein, and to support the container substantially unyieldingly, the container-receiving chamber comprising two end compartments receptive of opposed end sections of the container and separated by a constriction extending transversely across the width of the container-receiving chamber adjacent to the central portion thereof, said constriction being adapted to define a narrow passage of communication within the container between said end compartments, in the width of each end compartment of said container-receiving chamber, as taken in one of two orthogonal lateral projections, increasing gradually in a direction away from said constriction over a region adjoining said constriction and, as taken in the other of said lateral projections, increasing in a direction away from said constriction over said region, the perimeter of said container-receiving chamber, as taken in planes parallel to the directions of projection, being substantially the same as the perimeter of the blood container as taken at the same planes.

28. A device according to claim 27, at least one end of the container-receiving chamber having projection extending into the container receiving chamber towards the other end.

29. A device according to claim 27, including constricting means comprising at least one pinching device extending across the container-receiving chamber and adapted to engage and pinch the container at said constriction.

* * * * *